United States Patent
Dai et al.

(10) Patent No.: US 11,890,028 B1
(45) Date of Patent: Feb. 6, 2024

(54) VISUAL TWEEZER

(71) Applicant: HEIFENG ZHIZAO (SHENZHEN) TECHNOLOGY CO., LTD, Shenzhen (CN)

(72) Inventors: Bicheng Dai, Shenzhen (CN); Kunsheng Chen, Shenzhen (CN); Hongchu Li, Shenzhen (CN)

(73) Assignee: HEIFENG ZHIZAO (SHENZHEN) TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 18/351,045

(22) Filed: Jul. 12, 2023

(30) Foreign Application Priority Data

Jul. 14, 2022 (CN) .......................... 202221803417.8

(51) Int. Cl.
*A61B 17/30* (2006.01)
*A61B 1/04* (2006.01)

(52) U.S. Cl.
CPC ................ *A61B 17/30* (2013.01); *A61B 1/04* (2013.01)

(58) Field of Classification Search
CPC .................................. A61B 17/30; A61B 1/04
See application file for complete search history.

(56) References Cited

U.S. PATENT DOCUMENTS 9,167,959 B1 * 10/2015 Rubtsov ................ A61B 17/30
2020/0037858 A1 * 2/2020 Pedreira de Cerqueira Filho .......
A61B 18/14

FOREIGN PATENT DOCUMENTS

| CN | 112353560 A | * | 2/2021 | ............... A61B 1/04 |
| CN | 214338020 U | * | 10/2021 | |
| CN | 215651987 U | * | 1/2022 | |
| CN | 217020020 U | * | 7/2022 | |

* cited by examiner

*Primary Examiner* — Stephen A Vu
(74) *Attorney, Agent, or Firm* — Daniel M. Cohn; Howard M. Cohn

(57) ABSTRACT

A visual tweezer includes a main shell, a connecting shank, a tweezer assembly, a driving assembly, a circuit assembly and a camera assembly. The driving assembly including a press member, a push member, and a connector, wherein the push member is arranged on one side of the connecting shank close to the main shell; the connector is connected to the push member and is connected to the tweezer assembly through the second opening and the second storage cavity; the press member is abutted with the push member and is used for driving, when pressed by an external force, the push member to move in the preset direction, so that the connector moves in the preset direction to drive the tweezer assembly to be opened or closed. It can be convenient to control opening and closing of the tweezer, and operations of the user are facilitated.

9 Claims, 6 Drawing Sheets

VISUAL TWEEZER

CROSS-REFERENCE TO RELATED APPLICATIONS

The application claims priority of Chinese patent application CN202221803417.8, filed on Jul. 14, 2022, which is incorporated herein by reference in its entireties.

TECHNICAL FIELD

The present disclosure belongs to the field of personal hygiene, and more particularly, to a visual tweezer.

BACKGROUND

During use, a tweezer is usually manually controlled to be opened and closed to clamp and hold a target object, which heavily depends on the experience of an operator and the operability of the tweezer. As a result, it is hard to operate the existing tweezer in the oral cavity, the ear canal, the intestinal tract, or other complicated working conditions.

SUMMARY

In view of this, the present disclosure provides a visual tweezer, which can be conveniently controlled to be opened and closed. It is convenient for a user to operate the visual tweezer.

The present disclosure discloses a visual tweezer, which includes a main shell, a connecting shank, a tweezer assembly, a driving assembly, a circuit assembly and a camera assembly. The main shell provided with a first storage cavity and a first opening communicated with the first storage cavity. The connecting shank including a second storage cavity, a second opening communicated with one end of the second storage cavity, and a third opening communicated with the other end of the second storage cavity, wherein a direction from the second opening to the third opening is a preset direction. The tweezer assembly, arranged at the end, provided with the second opening, of the connecting shank. The driving assembly including a press member, a push member, and a connector, wherein the push member is arranged on one side of the connecting shank close to the main shell; the connector is connected to the push member and is connected to the tweezer assembly through the second opening and the second storage cavity; the press member is abutted with the push member and is used for driving, when pressed by an external force, the push member to move in the preset direction, so that the connector moves in the preset direction to drive the tweezer assembly to be opened or closed. The circuit assembly, arranged in the first storage cavity. The camera assembly is mounted at the third opening and electrically connected to the circuit assembly.

Compared with the prior art, according to the visual tweezer according to this embodiment of the present application, by the arrangement of the press member, the push member, and the connector, the press member drives, when pressed by an external force, the push member to move in the preset direction, so that the connector moves in the preset direction to drive the tweezer assembly to be opened or closed, and the user can control and operate the visual tweezer more conveniently, easily, and stably. Meanwhile, the visual tweezer is further provided with the camera assembly, so that use is facilitated, and the user can see an operation point clearly. The operation is more accurate, and the user experience is better.

In one embodiment of the present disclosure, the connecting shank includes a connecting shell and a connecting seat; the connecting shell is provided with the second storage cavity, the second opening, and the third opening; the connecting seat includes a connecting end arranged at the second opening and a guide portion connected to the connecting end; the push member sleeves a periphery of the guide portion; the connecting seat is further provided with a first through hole penetrating through the connecting end and the guide portion; the connector passes through the first through hole; the driving assembly further includes an elastic member; the elastic member sleeves the guide portion and is abutted between the push member and the main shell; when pressed by the external force, the press member drives the push member to move in the preset direction and compress the elastic member; and when the press member is released, the elastic member releases an elastic force to drive the push member, the connector, and the tweezer assembly to be reset.

By the arrangement of the elastic member, the press member, and the push member, when pressed by the external force, the press member can drive the push member to move in the preset direction and compress the elastic member, so that the tweezer assembly is opened; and when the press member is released, the elastic member can release the elastic force to drive the push member, the connector, and the tweezer assembly to be reset, so that the tweezer assembly is closed for clamping. The operation is simple, and it is convenient for the user to operate the visual tweezer.

In one embodiment of the present disclosure, the press member includes a first side wall structure which is annularly arranged; an inner surface of the first side wall structure has a first inclined surface inclined relative to the preset direction towards one side of the elastic member; the first side wall structure is further provided with a plurality of notches extending in the preset direction; openings of the plurality of notches face one side with the connecting shank and are annularly arranged around the first side wall structure; the push member includes a second side wall structure which is annularly arranged; an outer surface of the second side wall structure includes a first portion, a second portion, and a second inclined surface connected between the first portion and the second portion; the first inclined surface is abutted with the second inclined surface; and when the press member is pressed by an external force perpendicular to the preset direction, the first inclined surface presses the second inclined surface to drive the push member to move in the preset direction and compress the elastic member.

By the arrangement of the first inclined surface and the second inclined surface, when the press member is pressed by the external force perpendicular to the preset direction, the first inclined surface presses the second inclined surface to drive the push member to move in the preset direction and compress the elastic member, which completes the opening and closing operations performed on the tweezer assembly. The operation is simple, and it is convenient for the user to operate the visual tweezer.

In one embodiment of the present disclosure, the connecting shell includes a main body portion, a connecting plate, and a fixed end; the main body portion surrounds the second storage cavity; the connecting plate is connected to one end of the main body portion close to the second opening; the fixed end is connected to the connecting plate and extends in the preset direction towards one end away from the main body portion; the tweezer assembly is arranged at the fixed end; and the connector is connected to the tweezer assembly through the connecting plate.

In one embodiment of the present disclosure, the connecting shank includes a connecting shell and a connecting seat; the connecting shell is provided with the second storage cavity, the second opening, and the third opening; the connecting seat is away from one side of the connecting shell away from the tweezer assembly; the connecting seat includes a mounting notch; the mounting notch faces one side away from the connecting shell; the press member is mounted at the mounting notch; the main shell includes an outer shell provided with the first storage cavity and an inner shell arranged at the first storage cavity; the driving assembly further includes a guide member connected to the main shell and extending towards the connecting shank, a first elastic member, and a second elastic member; the push member sleeves a periphery of the guide member; the press member is abutted with the push member; the first elastic member is abutted between the press member and the connecting seat; the second elastic member is abutted between the inner shell and the push member; when pressed by the external force, the press member drives the push member to move in the preset direction and compress the first elastic member and the second elastic member; and when the press member is released, the first elastic member releases an elastic force to drive the press member to be reset, and the second elastic member releases an elastic force to drive the push member, the connector, and the tweezer assembly to be reset.

By the arrangement of the press member, the push member, the first elastic member, and the second elastic member, when pressed by the external force, the press member can drive the push member to move in the preset direction and compress the first elastic member and the second elastic member; and when the press member is released, the first elastic member can release the elastic force to drive the press member to be reset, and the second elastic member can release the elastic force to drive the push member, the connector, and the tweezer assembly to be reset, so that the opening and closing operations performed on the tweezer assembly are completed. The operation is simple, and it is convenient for the user to operate the visual tweezer.

In one embodiment of the present disclosure, the driving assembly is arranged in the second storage cavity; the outer shell is provided with an opening; the press member is exposed by the opening; the visual tweezer further include a flexible sleeve; the flexible sleeve sleeves one end of the outer shell close to the connecting shank and covers the press member; there are a plurality of the press members, openings, mounting notches, and first elastic members, which are in one-to-one correspondence; and the plurality of press members are annularly arranged around a periphery of the connecting seat.

Since there are the plurality of the press members, openings, mounting notches, and first elastic members, which are in one-to-one correspondence, and the plurality of press members are annularly arranged around a periphery of the connecting seat, a user can apply a pressure from multiple directions to control the visual tweezer to be opened and closed, and the pressure is uniform. The operation is simple, and it is convenient for the user to operate the visual tweezer.

In one embodiment of the present disclosure, the press member includes a first inclined surface inclined relative to the preset direction towards the push member; the push member is provided with a second inclined surface; the first inclined surface is abutted with the second inclined surface; when the press member is pressed by an external force perpendicular to the preset direction, the first elastic member is compressed; and the first inclined surface presses the second inclined surface to drive the push member to move in the preset direction and compress the second elastic member.

In one embodiment of the present disclosure, the tweezer assembly includes a first clamping portion, a second clamping portion, and a driving member; the driving member includes a connecting portion and a sliding portion; the connecting portion is connected to the connector; the sliding portion is provided with a first sliding portion and a second sliding portion which are inclined relative to the preset direction; the first clamping portion and the second clamping portion are rotatably connected to the fixed end respectively; the first clamping portion is provided with a third sliding portion cooperating with the first sliding portion; the second clamping portion is provided with a fourth sliding portion cooperating with the second sliding portion; and when the connector moves in the preset direction, the third sliding portion and the fourth sliding portion respectively slide along the first sliding portion and the second sliding portion, so that the first clamping portion and the second clamping portion rotate relative to the fixed end, and the tweezer assembly is switched from an opened state to a clamped state.

By the arrangement of the first sliding portion, the second sliding portion, the third sliding portion, and the fourth sliding portion, when the connector moves in the preset direction, the third sliding portion and the fourth sliding portion can respectively slide along the first sliding portion and the second sliding portion, so that the first clamping portion and the second clamping portion rotate relative to the fixed end, and the tweezer assembly is switched from the opened state to the clamped state. In the entire clamping operation process, the first clamping portion and the second clamping portion can be stably opened and closed, which ensures the stability and safety of the operation process.

In one embodiment of the present disclosure, the first clamping portion is provided with a first storage groove on one side close to the second clamping portion; the second clamping portion is provided with a second storage groove on one side close to the first clamping portion; in the clamped state, the first clamping portion abuts against the second clamping portion; the first storage groove is communicated to the second storage groove; the driving member is located in the first storage groove and the second storage groove; the first storage groove and the second storage groove are each provided with a first pivoting portion; the fixed end is provided with second pivoting portions corresponding to the first pivoting portions; the first pivoting portions is rotatably connected to the corresponding second pivoting portions; the visual tweezer further includes a flexible sleeve; and the flexible sleeve sleeves a periphery of the press member.

By the arrangement of the first storage groove and the second storage groove, the driving member can move in the first storage groove and the second storage groove, without contacting an operation point to cause influence or injury to the user. Furthermore, the visual tweezer can have a simpler structure and be convenient to operate. Meanwhile, the flexible sleeve sleeves the periphery of the press member, which can make an operation in a pressing process more convenient.

In one embodiment of the present disclosure, the visual tweezer further includes an electric connector; one end of the electric connector is electrically connected to the camera assembly, and is electrically connected to the circuit assembly through the second storage cavity and the driving assembly; the electric connector includes a first connecting section connected to the camera assembly, a second connecting section connected to the first connecting section, and a third connecting section connected to one end of the second connecting section away from the first connecting section; the second connecting section is connected between the first connecting section and the third connecting section in a bent manner; and the third connecting section is perpendicularly connected between the first connecting section and the second connecting section.

By the arrangement of the electric connector, all the elements of the visual tweezer can be electrically connected, so that the visual tweezer can have more functions and are more convenient to operate. Meanwhile, the electric connector is electrically connected to the circuit assembly through the second storage cavity and the driving assembly, so that the electric connection of the visual tweezer is safer.

BRIEF DESCRIPTION OF THE DRAWINGS

In order to explain the technical solutions of the embodiments of the present disclosure more clearly, the following will briefly introduce the accompanying drawings used in the embodiments. Apparently, the drawings in the following description are only some embodiments of the present disclosure. Those of ordinary skill in the art can obtain other drawings based on these drawings without creative work.

DETAILED DESCRIPTION OF THE EMBODIMENTS

Figure 1:
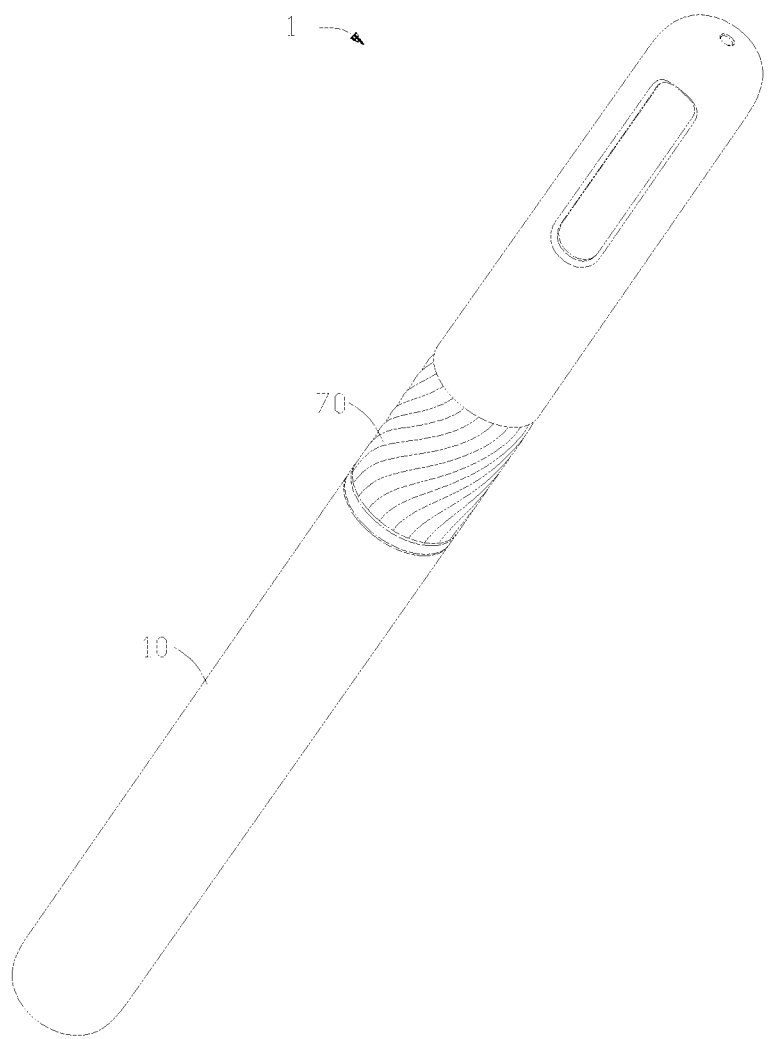
FIG. 1 is a three-dimensional diagram of a visual tweezer according to a first embodiment of the present disclosure.

In order to make the aims, technical solution and advantages of the present disclosure will be clearly, the present disclosure is further described below in combination with accompanying drawings and implementations. It should be understood that the specific embodiments described herein are intended only to explain the present disclosure and are not intended to define the present disclosure.

In addition, the terms "mounted", "disposed", "provided", "connected", "connected", and "socket" are to be construed broadly to mean, for example, a fixed connection, a detachable connection, or an integral construction; It may be a mechanical connection, or an electrical connection; The specific meaning of the above-mentioned terms in the present disclosure will be understood by those of ordinary skill in the art as the case may be, either directly, or indirectly, via an intermediate medium, or internal communication between two devices, elements, or components. The specific meanings of these terms in the present disclosure will be understood by those of ordinary skill in the art as the case may be.

In the present disclosure, the terms "upper", "lower", "left", "right", "front", "rear", "top", "bottom", "inner", "outer", "middle", "vertical", "horizontal", "transverse", "longitudinal", and the like indicate azimuth or positional relationships based primarily on the azimuth or positional relationships shown in the drawings, Not intended to define the indicated device, element or component must have a particular orientation, or be constructed and operated in a particular orientation.

Figure 2:
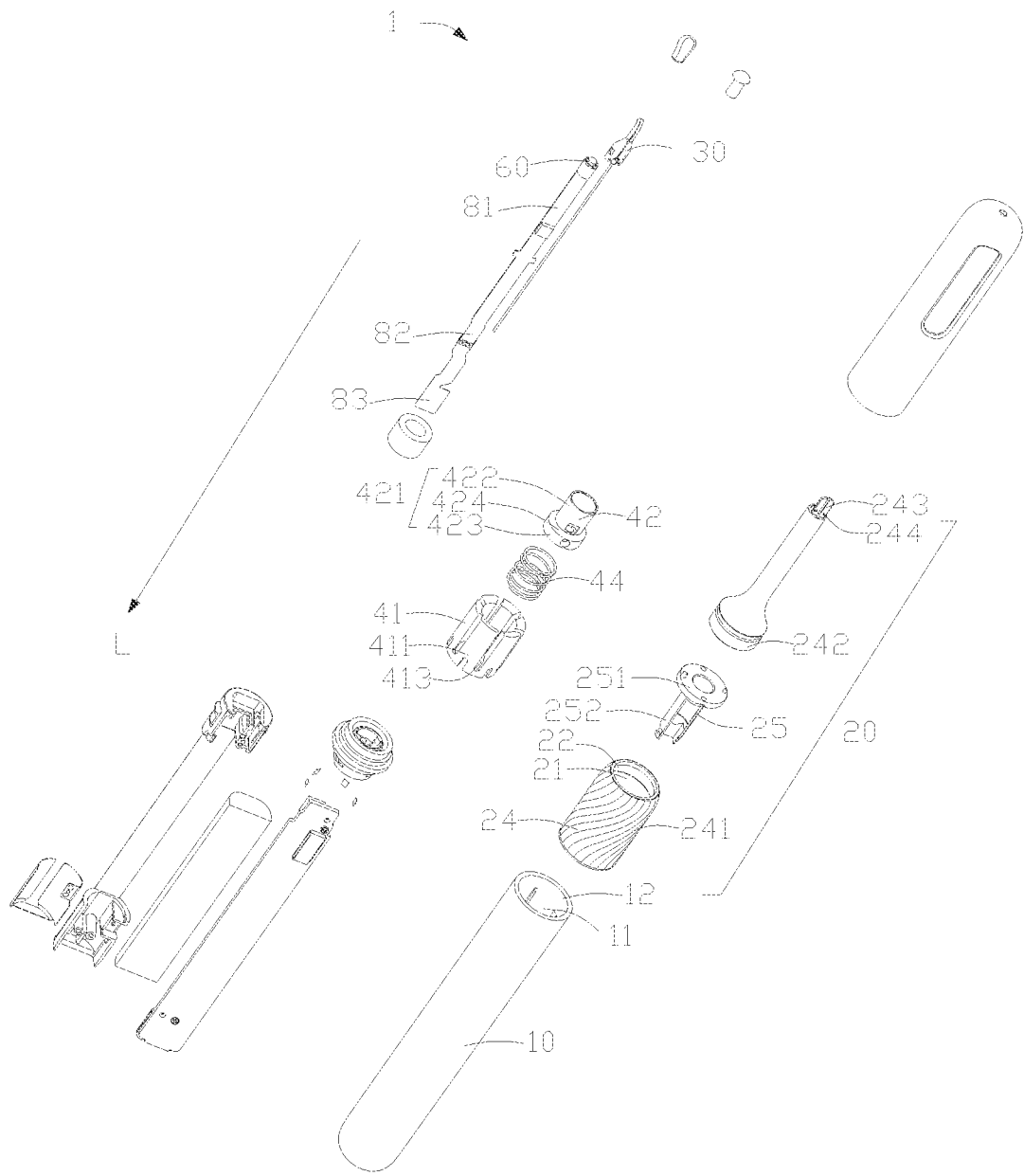
FIG. 2 is an exploded diagram of the visual tweezer shown in FIG. 1.
Figure 3:
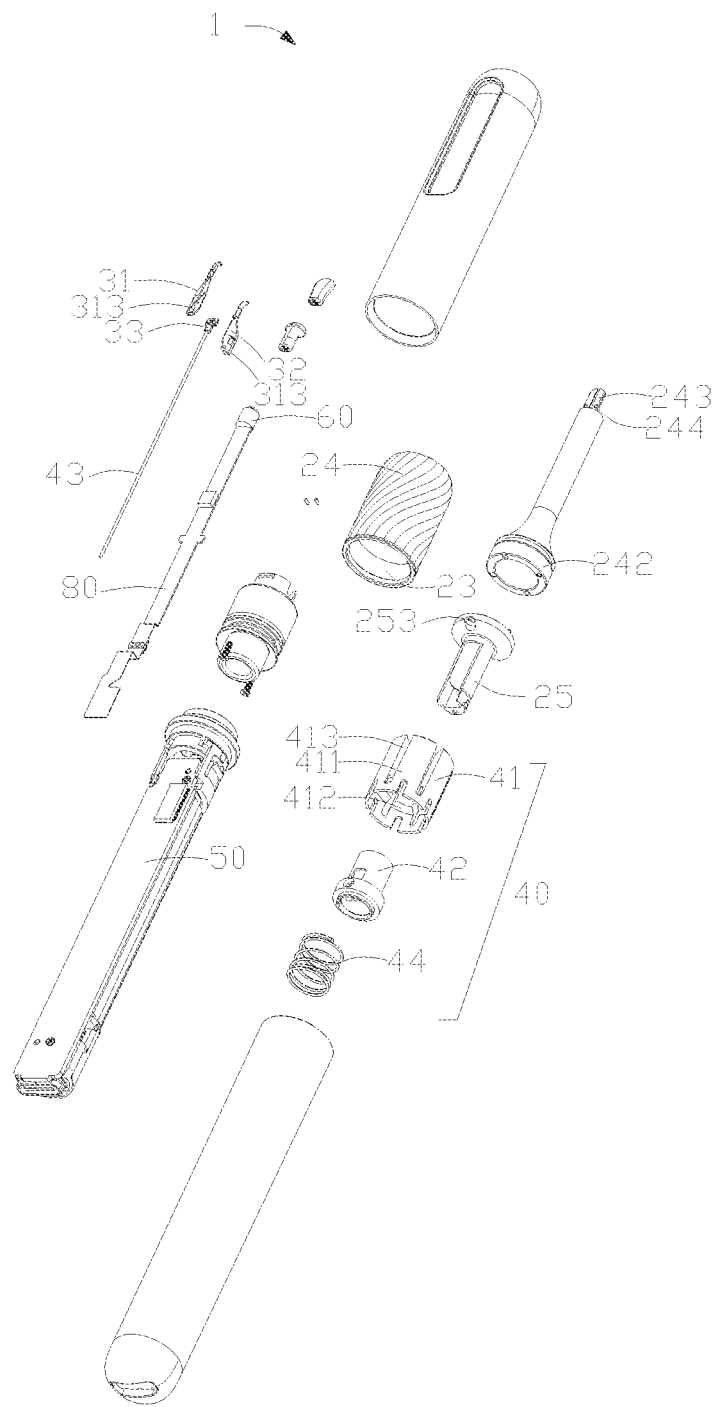
FIG. 3 is an exploded diagram of the visual tweezer shown in FIG. 1 in another angle.
Figure 4:
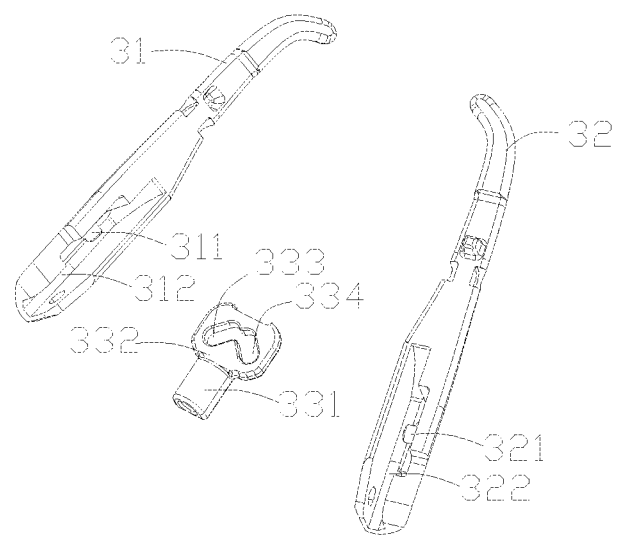
FIG. 4 is an exploded diagram of a tweezer assembly of the visual tweezer shown in FIG. 1.

Referring to FIG. 1 to FIG. 4, FIG. 1 is a three-dimensional diagram of a visual tweezer 1 according to a first embodiment of the present disclosure; FIG. 2 is an exploded diagram of the visual tweezer 1 shown in FIG. 1; FIG. 3 is an exploded diagram of the visual tweezer 1 shown in FIG. 1 in another angle; and FIG. 4 is an exploded diagram of a tweezer assembly 30 of the visual tweezer 1 shown in FIG. 1. An embodiment of the present disclosure provides a visual tweezer 1. The visual tweezer 1 is applicable to a visual otoscope, a visual ear picking rod, a visual mouth mirror, a visual dental flosser, and the like, and can be used for clamping debris in the ear canal, the oral cavity, and a crevice between teeth. In this embodiment, by way example, the visual tweezer 1 is applied to the visual ear picking rod for description.

A main shell 10 is provided with a first storage cavity 11 and a first opening 12 communicated with the first storage cavity 11. A connecting shank 20 includes a second storage cavity 21, a second opening 22 communicated with one end of the second storage cavity 21, and a third opening 23 communicated with the other end of the second storage cavity 21. A direction from the second opening 22 to the third opening 23 is a preset direction L. A tweezer assembly 30 is arranged at the end, provided with the second opening 22, of the connecting shank 20. A driving assembly 40 includes a press member 41, a push member 42, and a connector 43. The push member 42 is arranged on one side of the connecting shank 20 close to the main shell 10. The connector 43 is connected to the push member 42 and is connected to the tweezer assembly 30 through the second opening 22 and the second storage cavity 21. The press member 41 is abutted with the push member 42 and is used for driving, when pressed by an external force, the push member 42 to move in the preset direction L, so that the connector 43 moves in the preset direction L to drive the tweezer assembly 30 to be opened or closed. A circuit assembly 50 is arranged in the first storage cavity 11. A camera assembly 60 is mounted at the third opening 23 and electrically connected to the circuit assembly 50.

It can be understood that in an ear picking process, a user or an operator can observe conditions in the ear canal through the camera assembly 60 on the visual tweezer 1. When debris needing to be picked up is found, the user or operator presses the press member 41 to drive the push member 42 to move in the preset direction L, so that the connector 43 moves in the preset direction L to drive the tweezer assembly 30 to be opened or closed, thereby accurately clamping the debris in the ear canal.

According to the visual tweezer 1 according to this embodiment of the present application, by the arrangement of the press member 41, the push member 42, and the connector 43, the press member 41 drives, when pressed by an external force, the push member 42 to move in the preset direction L, so that the connector 43 moves in the preset direction L to drive the tweezer assembly 30 to be opened or closed, and the user can control and operate the visual tweezer 1 more conveniently, easily, and stably. Meanwhile, the visual tweezer 1 is further provided with the camera assembly 60, so that use is facilitated, and the user can see an operation point clearly. The operation is more accurate, and the user experience is better.

Further, the connecting shank 20 includes a connecting shell 24 and a connecting seat 25. The connecting shell 24 is provided with a second storage cavity 21, a second opening 22, and a third opening 23. The connecting seat 25 includes a connecting end 251 arranged at the second opening 22 and a guide portion 252 connected to the connecting end 251. The push member 42 sleeves a periphery of the guide portion 252. The connecting seat 25 is further provided with a first through hole 253 penetrating through the connecting end 251 and the guide portion 252. The connector 43 passes through the first through hole 253. The driving assembly 40 further includes an elastic member 44. The elastic member 44 sleeves the guide portion 252 and is abutted between the push member 42 and the main shell 10. When pressed by the external force, the press member 41 can drive the push member 42 to move in the preset direction L and compress the elastic member 44; and when the press member 41 is released, the elastic member 44 can release an elastic force to drive the push member 42, the connector 43, and the tweezer assembly 30 to be reset. By the arrangement of the elastic member 44, the press member 41, and the push member 42, when pressed by the external force, the press member 41 can drive the push member 42 to move in the preset direction L and compress the elastic member 44, so that the tweezer assembly 30 is opened; and when the press member 41 is released, the elastic member 44 can release the elastic force to drive the push member 42, the connector 43, and the tweezer assembly 30 to be reset, so that the tweezer assembly 30 is closed for clamping. The operation is simple, and it is convenient for the user to operate the visual tweezer.

Further, the press member 41 includes a first side wall structure 411 which is annularly arranged. An inner surface of the first side wall structure 411 has a first inclined surface 412 inclined relative to the preset direction L towards one side of the elastic member 44. The first side wall structure 411 is further provided with a plurality of notches 413 extending in the preset direction L. Openings 15 of the plurality of notches 413 face one side with the connecting shank 20 and are annularly arranged around the first side wall structure 411. The push member 42 includes a second side wall structure 421 which is annularly arranged. An outer surface of the second side wall structure 421 includes a first portion 422, a second portion 423, and a second inclined surface 424 connected between the first portion 422 and the second portion 423. The first inclined surface 412 is abutted with the second inclined surface 424. When the press member 41 is pressed by an external force perpendicular to the preset direction L, the first inclined surface 412 presses the second inclined surface 424 to drive the push member 42 to move in the preset direction L and compress the elastic member 44. By the arrangement of the first inclined surface 412 and the second inclined surface 424, when the press member 41 is pressed by the external force perpendicular to the preset direction L, the first inclined surface 412 presses the second inclined surface 424 to drive the push member 42 to move in the preset direction L and compress the elastic member 44, which completes the opening and closing operations performed on the tweezer assembly 30. The operation is simple, and it is convenient for the user to operate the visual tweezer.

Further, the connecting shell 24 includes a main body portion 241, a connecting plate 242, and a fixed end 243. The main body portion 241 surrounds the second storage cavity 21. The connecting plate 242 is connected to one end of the main body portion 241 close to the second opening 22. The fixed end 243 is connected to the connecting plate 242 and extends in the preset direction L towards one end away from the main body portion 241. The tweezer assembly 30 is arranged at the fixed end 243. The connector 43 is connected to the tweezer assembly 30 through the connecting plate 242.

Further, the tweezer assembly 30 includes a first clamping portion 31, a second clamping portion 32, and a driving member 33. The driving member 33 includes a connecting portion 331 and a sliding portion 332. The connecting portion 331 is connected to the connector 43. The sliding portion 332 is provided with a first sliding portion 333 and a second sliding portion 334 which are inclined relative to the preset direction L. The first clamping portion 31 and the second clamping portion 32 are rotatably connected to the fixed end 243 respectively. The first clamping portion 31 is provided with a third sliding portion 311 cooperating with the first sliding portion 333. The second clamping portion 32 is provided with a fourth sliding portion 321 cooperating with the second sliding portion 334. When the connector 43 moves in the preset direction L, the third sliding portion 311 and the fourth sliding portion 321 respectively slide along the first sliding portion 333 and the second sliding portion 334, so that the first clamping portion 31 and the second clamping portion 32 rotate relative to the fixed end 243, and the tweezer assembly 30 is switched from an opened state to a clamped state. By the arrangement of the first sliding portion 333, the second sliding portion 334, the third sliding portion 311, and the fourth sliding portion 321, when the connector 43 moves in the preset direction L, the third sliding portion 311 and the fourth sliding portion 321 can respectively slide along the first sliding portion 333 and the second sliding portion 334, so that the first clamping portion 31 and the second clamping portion 32 rotate relative to the fixed end 243, and the tweezer assembly 30 is switched from the opened state to the clamped state. In the entire clamping operation process, the first clamping portion 31 and the second clamping portion 32 can be stably opened and closed, which ensures the stability and safety of the operation process.

Further, the first clamping portion 31 is provided with a first storage groove 312 on one side close to the second clamping portion 32. The second clamping portion 32 is provided with a second storage groove 322 on one side close to the first clamping portion 31. In the clamped state, the first clamping portion 31 abuts against the second clamping portion 32; the first storage groove 312 is communicated to the second storage groove 322; and the driving member 33 is located in the first storage groove 312 and the second storage groove 322. The first storage groove 312 and the second storage groove 322 are each provided with a first pivoting portion 313. The fixed end 243 is provided with second pivoting portions 244 corresponding to the first pivoting portions 313. The first pivoting portions 313 is rotatably connected to the corresponding second pivoting portions 244. The visual tweezer 1 further includes a flexible sleeve 70. The flexible sleeve 70 sleeves a periphery of the press member 41. By the arrangement of the first storage groove 312 and the second storage groove 322, the driving member 33 can move in the first storage groove 312 and the second storage groove 322, without contacting an operation point to cause influence or injury to the user. Furthermore, the visual tweezer 1 can have a simpler structure and be convenient to operate. Meanwhile, the flexible sleeve 70 sleeves the periphery of the press member 41, which can make an operation in a pressing process more convenient.

Further, the visual tweezer 1 further includes an electric connector. One end of the electric connector 80 is electrically connected to the camera assembly 60, and is electrically connected to the circuit assembly 50 through the second storage cavity 21 and the driving assembly 40. The electric connector 80 includes a first connecting section 81 connected to the camera assembly 60, a second connecting section 82 connected to the first connecting section 81, and a third connecting section 83 connected to one end of the second connecting section 82 away from the first connecting section 81. The second connecting section 82 is connected between the first connecting section 81 and the third connecting section 83 in a bent manner. The second connecting section 82 is perpendicularly connected between the first connecting section 81 and the third connecting section 83. By the arrangement of the electric connector 80, all the elements of the visual tweezer 1 can be electrically connected, so that the visual tweezer 1 can have more functions and are more convenient to operate. Meanwhile, the electric connector 80 is electrically connected to the circuit assembly 50 through the second storage cavity 21 and the driving assembly 40, so that the electric connection of the visual tweezer 1 is safer.

Figure 5:
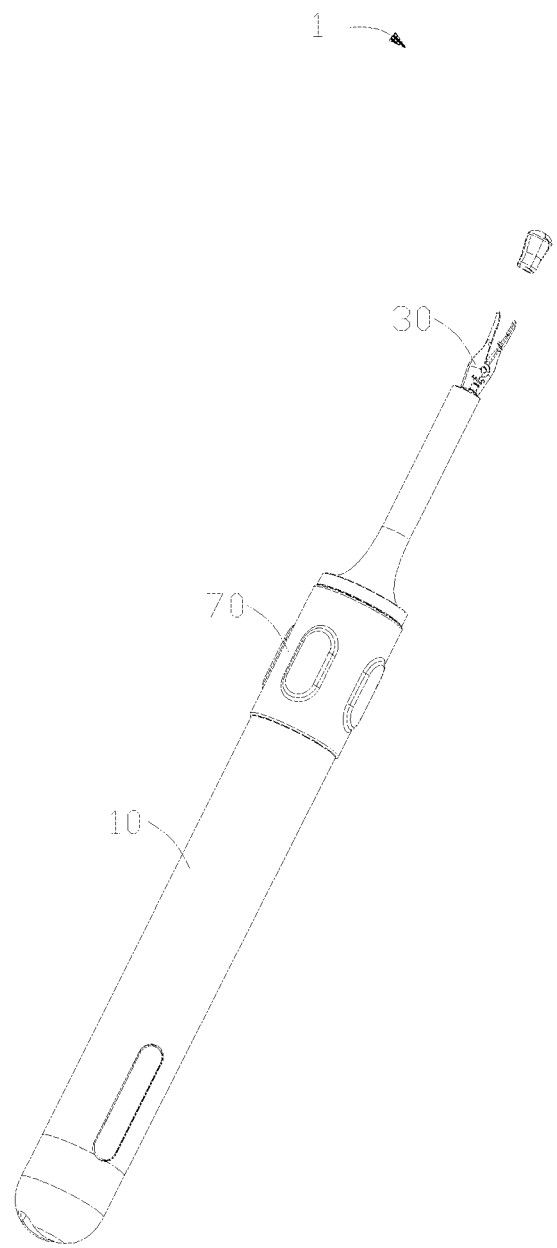
FIG. 5 is a three-dimensional diagram of a visual tweezer according to a second embodiment of the present disclosure.
Figure 6:
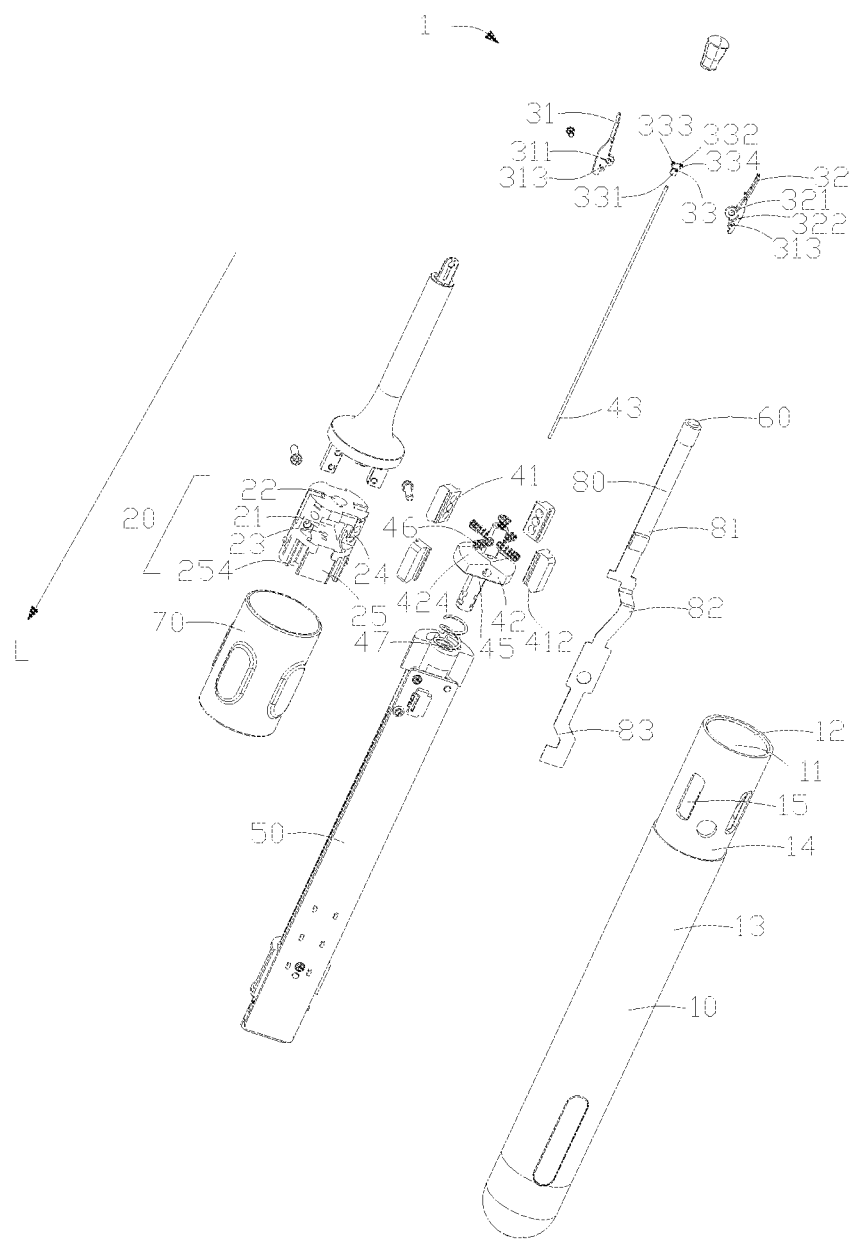
FIG. 6 is an exploded diagram of the visual tweezer shown in FIG. 5.

In some other embodiments, referring to FIG. 5 to FIG. 6, FIG. 5 is a three-dimensional diagram of visual tweezer 1 according to a second embodiment of the present disclosure; and FIG. 6 is an exploded diagram of the visual tweezer 1 shown in FIG. 5. In this embodiment, the visual tweezer 1 are basically the same as the visual tweezer 1 in the above embodiment. That is, the descriptions of the visual tweezer 1 in the above embodiment is also basically applicable to the visual tweezer 1 of this embodiment. Differences between the visual tweezer 1 of this embodiment and the visual tweezer 1 in the above embodiment are mainly described below.

The connecting shank 20 includes a connecting shell 24 and a connecting seat 25. The connecting shell 24 is provided with a second storage cavity 21, a second opening 22, and a third opening 23. The connecting seat 25 is away from one side of the connecting shell 24 away from the tweezer assembly 30. The connecting seat 25 includes a mounting notch 254. The mounting notch 254 faces one side away from the connecting shell 24. The press member 41 is mounted at the mounting notch 254. The main shell 10 includes an outer shell 13 provided with a first storage cavity 11 and an inner shell 14 arranged at the first storage cavity 11. The driving assembly 40 further includes a guide member 45 connected to the main shell 10 and extending towards the connecting shank 20, a first elastic member 46, and a second elastic member 47. The push member 42 sleeves a periphery of the guide member 45. The press member 41 is abutted with the push member 42. The first elastic member 46 is abutted between the press member 41 and the connecting seat 25. The second elastic member 47 is abutted between the inner shell 14 and the push member 42. When pressed by an external force, the press member 41 can drive the push member 42 to move in a preset direction L and compress the first elastic member 46 and the second elastic member 47; and when the press member 41 is released, the first elastic member 46 can release an elastic force to drive the press member 41 to be reset, and the second elastic member 47 can release an elastic force to drive the push member 42, the connector 43, and the tweezer assembly 30 to be reset. By the arrangement of the press member 41, the push member 42, the first elastic member 46, and the second elastic member 47, when pressed by the external force, the press member 41 can drive the push member 42 to move in the preset direction L and compress the first elastic member 46 and the second elastic member 47; and when the press member 41 is released, the first elastic member 46 can release the elastic force to drive the press member 41 to be reset, and the second elastic member 47 can release the elastic force to drive the push member 42, the connector 43, and the tweezer assembly 30 to be reset, so that the opening and closing operations performed on the tweezer assembly 30 are completed. The operation is simple, and it is convenient for the user to operate the visual tweezer.

Further, the driving assembly 40 is arranged in the second storage cavity 21. The outer shell 13 is provided with an opening 15. The press member 41 is exposed by the opening 15. The visual tweezer 1 further include a flexible sleeve 70. The flexible sleeve 70 sleeves one end of the outer shell 13 close to the connecting shank 20 and covers the press member 41. There are a plurality of the press members 41, openings 15, mounting notches 254, and first elastic members 46, which are in one-to-one correspondence. The plurality of press members 41 are annularly arranged around a periphery of the connecting seat 25. Since there are the plurality of the press members 41, openings 15, mounting notches 254, and first elastic members 46, which are in one-to-one correspondence, and the plurality of press members 41 are annularly arranged around a periphery of the connecting seat 25, a user can apply a pressure from multiple directions to control the visual tweezer 1 to be opened and closed, and the pressure is uniform. The operation is simple, and it is convenient for the user to operate the visual tweezer.

Further, the press member 41 includes a first inclined surface 412 inclined relative to the preset direction L towards the push member 42. The push member 42 is provided with a second inclined surface 424. The first inclined surface 412 is abutted with the second inclined surface 424. When the press member 41 is pressed by an external force perpendicular to the preset direction L, the first elastic member 46 is compressed; and the first inclined surface 412 presses the second inclined surface 424 to drive the push member 42 to move in the preset direction L and compress the second elastic member 47. By the arrangement of the first inclined surface 412 and the second inclined surface 424, when the press member 41 is pressed by the external force perpendicular to the preset direction L, the first elastic member 46 is compressed, and the first inclined surface 412 presses the second inclined surface 424 to drive the push member 42 to move in the preset direction L and compress the elastic member 47, which completes the opening and closing operations performed on the tweezer assembly 30. The operation is simple, and it is convenient for the user to operate the visual tweezer.

One or more implementation modes are provided above in combination with specific contents, and it is not deemed that the specific implementation of the present disclosure is limited to these specifications. Any technical deductions or replacements approximate or similar to the method and structure of the present disclosure or made under the concept of the present disclosure shall fall within the scope of protection of the present disclosure.

What is claimed is:
1. A visual tweezer, comprising:
a main shell, provided with a first storage cavity and a first opening communicated with the first storage cavity;
a connecting shank, comprising a second storage cavity, a second opening communicated with one end of the second storage cavity, and a third opening communicated with another end of the second storage cavity, wherein a direction from the second opening to the third opening is a preset direction;
a tweezer assembly, arranged at the end, provided with the second opening, of the connecting shank;

a driving assembly, comprising a press member, a push member, and a connector, wherein the push member is arranged on one side of the connecting shank close to the main shell; the connector is connected to the push member and is connected to the tweezer assembly through the second opening and the second storage cavity; the press member is abutted with the push member and is used for driving, when pressed by an external force, the push member to move in the preset direction, so that the connector moves in the preset direction to drive the tweezer assembly to be opened or closed;

a circuit assembly, arranged in the first storage cavity; and a camera assembly, mounted at the third opening and electrically connected to the circuit assembly;

wherein the connecting shank comprises a connecting shell and a connecting seat; the connecting shell is provided with the second storage cavity, the second opening, and the third opening; the connecting seat comprises a connecting end arranged at the second opening and a guide portion connected to the connecting end; the push member sleeves a periphery of the guide portion; the connecting seat is further provided with a first through hole penetrating through the connecting end and the guide portion; the connector passes through the first through hole; the driving assembly further comprises an elastic member; the elastic member sleeves the guide portion and is abutted between the push member and the main shell; when pressed by the external force, the press member drives the push member to move in the preset direction and compress the elastic member; and when the press member is released, the elastic member releases an elastic force to drive the push member, the connector, and the tweezer assembly to be reset.

2. The visual tweeze-s-tweezer according to claim 1, wherein the press member comprises a first side wall structure which is annularly arranged; an inner surface of the first side wall structure has a first inclined surface inclined relative to the preset direction towards one side of the elastic member; the first side wall structure is further provided with a plurality of notches extending in the preset direction; openings of the plurality of notches face one side with the connecting shank and are annularly arranged around the first side wall structure; the push member comprises a second side wall structure which is annularly arranged; an outer surface of the second side wall structure comprises a first portion, a second portion, and a second inclined surface connected between the first portion and the second portion; the first inclined surface is abutted with the second inclined surface; and when the press member is pressed by an external force perpendicular to the preset direction, the first inclined surface presses the second inclined surface to drive the push member to move in the preset direction and compress the elastic member.

3. The visual tweezer according to claim 1, wherein the connecting shell comprises a main body portion, a connecting plate, and a fixed end; the main body portion surrounds the second storage cavity; the connecting plate is connected to one end of the main body portion close to the second opening; the fixed end is connected to the connecting plate and extends in the preset direction towards one end away from the main body portion; the tweezer assembly is arranged at the fixed end; and the connector is connected to the tweezer assembly through the connecting plate.

4. The visual tweezer according to claim 3, wherein the tweezer assembly comprises a first clamping portion, a second clamping portion, and a driving member; the driving member comprises a connecting portion and a sliding portion; the connecting portion is connected to the connector; the sliding portion is provided with a first sliding portion and a second sliding portion which are inclined relative to the preset direction; the first clamping portion and the second clamping portion are rotatably connected to the fixed end respectively; the first clamping portion is provided with a third sliding portion cooperating with the first sliding portion; the second clamping portion is provided with a fourth sliding portion cooperating with the second sliding portion; and when the connector moves in the preset direction, the third sliding portion and the fourth sliding portion respectively slide along the first sliding portion and the second sliding portion, so that the first clamping portion and the second clamping portion rotate relative to the fixed end, and the tweezer assembly is switched from an opened state to a clamped state.

5. The visual tweezer according to claim wherein the first clamping portion is provided with a first storage groove on one side close to the second clamping portion; the second clamping portion is provided with a second storage groove on one side close to the first clamping portion; in the clamped state, the first clamping portion abuts against the second clamping portion; the first storage groove is communicated to the second storage groove; the driving member is located in the first storage groove and the second storage groove; the first storage groove and the second storage groove are each provided with a first pivoting portion; the fixed end is provided with second pivoting portions corresponding to the first pivoting portions; the first pivoting portions is rotatably connected to the corresponding second pivoting portions; the visual tweezer further comprises a flexible sleeve; and the flexible sleeve sleeves a periphery of the press member.

6. The visual tweezer according to claim 1, wherein the connecting shank comprises a connecting shell and a connecting seat; the connecting shell is provided with the second storage cavity, the second opening, and the third opening; the connecting seat is away from one side of the connecting shell away from the tweezer assembly; the connecting seat comprises a mounting notch; the mounting notch faces one side away from the connecting shell; the press member is mounted at the mounting notch; the main shell comprises an outer shell provided with the first storage cavity and an inner shell arranged at the first storage cavity; the driving assembly further comprises a guide member connected to the main shell and extending towards the connecting shank, a first elastic member, and a second elastic member; the push member sleeves a periphery of the guide member; the press member is abutted with the push member; the first elastic member is abutted between the press member and the connecting seat; the second elastic member is abutted between the inner shell and the push member; when pressed by the external force, the press member drives the push member to move in the preset direction and compress the first elastic member and the second elastic member; and when the press member is released, the first elastic member releases an elastic force to drive the press member to be reset, and the second elastic member releases an elastic force to drive the push member, the connector, and the tweezer assembly to be reset.

7. The visual tweezer according to claim 6, wherein the driving assembly is arranged in the second storage cavity; the outer shell is provided with an opening; the press member is exposed by the opening; the visual tweezer further comprises a flexible sleeve; the flexible sleeve sleeves one end of the outer shell close to the connecting shank and covers the press member; there are a plurality of the press members, openings, mounting notches, and first elastic members, which are in one-to-one correspondence; and the plurality of press members are annularly arranged around a periphery of the connecting seat.

8. The visual tweezer according to claim 6, wherein the press member comprises a first inclined surface inclined relative to the preset direction towards the push member; the push member is provided with a second inclined surface; the first inclined surface is abutted with the second inclined surface; when the press member is pressed by an external force perpendicular to the preset direction, the first elastic member is compressed; and the first inclined surface presses the second inclined surface to drive the push member to move in the preset direction and compress the second elastic member.

9. A visual tweezer, comprising:
a main shell, provided with a first storage cavity and a first opening communicated with the first storage cavity;
a connecting shank, comprising a second storage cavity, a second opening communicated with one end of the second storage cavity, and a third opening communicated with another end of the second storage cavity, wherein a direction from the second opening to the third opening is a preset direction;
a tweezer assembly, arranged at the end, provided with the second opening, of the connecting shank;
a driving assembly, comprising a press member, a push member, and a connector, wherein the push member is arranged on one side of the connecting shank close to the main shell: the connector is connected to the push member and is connected to the tweezer assembly through the second opening and the second storage cavity; the press member is abutted with the push member and is used for driving, when pressed by an external force, the push member to move in the preset direction, so that the connector moves in the preset direction to drive the tweezer assembly to be opened or closed;
a circuit assembly, arranged in the first storage cavity; and
a camera assembly, mounted at the third opening and electrically connected to the circuit assembly;
wherein the visual tweezer further comprises an electric connector; one end of the electric connector is electrically connected to the camera assembly, and is electrically connected to the circuit assembly through the second storage cavity and the driving assembly; the electric connector comprises a first connecting section connected to the camera assembly, a second connecting section connected to the first connecting section, and a third connecting section connected to one end of the second connecting section away from the first connecting section; the second connecting section is connected between the first connecting section and the third connecting section in a bent manner; and the second connecting section is perpendicularly connected between the first connecting section and the third connecting section.

\* \* \* \* \*